US005199430A

United States Patent [19]
Fang et al.

[11] Patent Number: 5,199,430
[45] Date of Patent: Apr. 6, 1993

[54] MICTURITIONAL ASSIST DEVICE

[75] Inventors: Zi-Ping Fang, University Hts.; J. Thomas Mortimer; Graham H. Creasey, both of Cleveland Hts., all of Ohio

[73] Assignee: Case Western Reserve University, Cleveland, Ohio

[21] Appl. No.: 667,523

[22] Filed: Mar. 11, 1991

[51] Int. Cl.$^5$ .............................. A61N 1/36
[52] U.S. Cl. ..................... 128/419 E; 128/419 R; 128/784
[58] Field of Search ............... 128/419 E, 419 R, 784, 128/885, 386, 788, 842, 843

[56] References Cited

U.S. PATENT DOCUMENTS

| | | | |
|---|---|---|---|
| 3,727,616 | 4/1973 | Lenzkes | 128/419 E |
| 3,870,051 | 3/1975 | Brindley | 128/419 E |
| 4,590,946 | 5/1986 | Loeb | 128/784 |
| 4,602,624 | 7/1986 | Naples et al. | 128/784 |
| 4,607,639 | 8/1986 | Tanagho et al. | 128/419 E |
| 4,608,985 | 9/1986 | Crish et al. | 128/419 R |
| 4,628,942 | 12/1986 | Sweeney et al. | 128/784 |
| 4,632,116 | 12/1986 | Rosen et al. | 128/419 R |
| 4,649,936 | 3/1987 | Ungar et al. | 128/784 |
| 4,739,764 | 4/1988 | Lue et al. | 128/419 E |

OTHER PUBLICATIONS

A Method for Attaining Natural Recruitment Order in Articifially Activated Muscles; Zi-Ping Fang and J. Thomas Mortimer; IEEE/Ninth Annual Conference of the Engineering in Medicine and Biology Society; 1977.
A Technique for Collision Block of Peripheral Nerve: Single Stimulus Analysis van den Honert and J. Thomas Mortimer; IEEE Transactions of Biomedical Engineering; vol. BME-28, No. 5, May 1981.
A Technique for Collision Block of Peripheral Nerve: Frequency Dependence van den Honert and J. Thomas Mortimer; IEEE Transactions of Biomedical Engineering; vol. BME-28, No. 5, May 1981.
Generation of Unidirectionally Propagated Action Potentials in a Peripheral Nerve by Brief Stimuli; van den Honert and J. Thomas Mortimer; American Association for the Advancement of Science; Reprint Series Dec. 14, 1979; vol. 206.
Alternating Motor Unit Activation in Electrically Stimulated Muscles; Zi-Ping Fang and J. Thomas Mortimer; 1988 World Congress on Medical Physics and Biomedical Engineering; vol. 33; Supplement I; 1988.
Selective Activation of Small Motor Axons by Spiral Cuff Electrode and Quasi-Trapezoidal Stimulus Pulses; Zi-Ping Fang and J. Thomas Mortimer; Abstracts; Society for Neuroscience 17th Annual Meeting; 13 Part 3; 1987.
Gray's Anatomy; Edited by Williams, et al.; 37th Edition; Churchill Livingstone; 1989; pp. 1143-1145 and 1416-1424.

Primary Examiner—William E. Kamm
Assistant Examiner—Kennedy J. Schaetzle
Attorney, Agent, or Firm—Fay, Sharpe, Beall, Fagan, Minnich & McKee

[57] ABSTRACT

Cuff electrodes (40a, 40b) are surgically implanted around S3 sacral ventral root nerve trunks (16a, 16b). The sacral ventral roots have smaller diameter nerve fibers (20a, 20b) which convey action potentials to cause detrusor activation to contract the bladder (10) and larger diameter nerve fibers (18a, 18 b) which carry action potentials for causing contraction of a urethral sphincter (12) to block the flow of urine from the bladder. A current source (50) causes current pulses (52) between such electrical contacts (46, 48) and a central electrical contact (44). The current pulses have an appropriate amplitude and waveform to initiate action potentials adjacent the central contact and to block the propagation of action potentials adjacent the end electrodes along the larger diameter nerve fibers (which have fewer nodes between the contacts) but not the smaller diameter nerve fibers (which have more nodes between the electrodes). In this manner, action potentials are electrically excited to propagate at least downstream on the smaller diameter nerve fibers causing contraction of the bladder. Concurrently, blocking action potentials are allowed to propagate upstream on at least the larger diameter nerve fibers, collision blocking naturally occurring action potentials propagating downstream. The transmission of action potentials downstream on the larger diameter nerve fibers is blocked by the current pulses allowing the urinary sphincter to relax.

13 Claims, 2 Drawing Sheets

MICTURITIONAL ASSIST DEVICE

BACKGROUND OF THE INVENTION

The present invention relates to the art of selective nerve stimulation. The invention finds particular application in conjunction with urination control and will be described with particular reference thereto. It is to be appreciated that the invention is also applicable to control systems for fecal incontinence, penile erection, and others.

The organs involved in bladder, bowel, and sexual function receive much of their control via the second, third, and fourth sacral nerves ($S_2$, $S_3$, and $S_4$). While one level of roots usually predominates for a particular function, there is considerable overlap. For example, the $S_3$ sacral nerve is the main stimulus for both bladder and rectal wall contraction. Bladder and rectal wall both receive some control also from $S_4$ and/or $S_2$ sacral nerves. Sphincters are probably mainly innervated by $S_4$, although the urethral sphincter has significant contributions from $S_3$. Hence, there is difficulty in applying artificial stimulus to contract the bladder without contracting the urethral sphincter and to contract the rectum without contracting the anal sphincter.

The external urethral sphincter receives stimulation on the sacral ventral roots to cause contraction to block urine flow. To discharge the bladder, in a healthy person, the bladder detrusor muscles are contracted to expel urine simultaneously with relaxing the urethral sphincter to allow the passage of the urine. The contraction of the bladder is also controlled by the sacral ventral roots. More specifically, contraction of the bladder detrusor muscles is caused by smaller diameter $S_3$ nerves and contraction of the urethral sphincter is controlled by predominantly larger diameter $S_3$ nerves as well as by $S_2$ and $S_4$ nerves which are intermixed in same roots.

Previously, electrical stimulation has been applied to control the bladder and bowel. The previous attempts have focused on three techniques: direct stimulation of the detrusor muscle, activation of the detrusor by stimulation of the conus medullaris, and activation of the detrusor by sacral root or nerve stimulation with extensive dorsal rhizotomy. All three of these methods suffer from the same problem. They all cause contraction of the bladder to expel urine concurrently with contraction of the external urethral sphincter blocking urine flow. The rhizotomy technique also results in the loss of erection for the male. It would be advantageous if contraction of the sphincter could be selectively blocked.

Techniques that are available for blocking nerve impulses are discussed, for example, in "A Technique for Collision Block of Peripheral Nerve: Single Stimulation Analysis", van den Honert and Mortimer, IEEE Transactions on Biomedical Engineering, Vol. BME-28, No. 5, May 1981, pages 373-378 and "Generation of Unidirectionally Propagated Action Potentials in a Peripheral Nerve by Brief Stimuli", van den Honert and Mortimer, Science, Vol. 206, December 1979, pages 1311-1312. With the van den Honert and Mortimer techniques, a nerve impulse or action potential is generated which travels toward the brain. When the artificially generated nerve impulse meets a motor impulse travelling from the brain, the motor impulse is collision blocked. That is, the artificially generated action potential cancels the motor action potential. If one were to apply the van den Honert and Mortimer techniques, it could be used to cause concurrent relaxation of both the bladder contracting muscles and the urethral sphincter. Again, the bladder contracting muscles and the urethral sphincter are operating at cross purposes.

A technique for fatigue resistant flexing of muscles of laboratory animals, particularly feline hind leg muscles, is described in "A Method for Attaining Natural Recruitment Order in Artificially Activated Muscles", Zi-Ping Fang and J. Thomas Mortimer, IEEE Ninth Annual Conference of the Engineering in Medicine and Biology Society, 1987. By way of background, applying an electrical potential (or current) of an appropriate amplitude along the length of a nerve causes an action potential to propagate in both directions from the stimulus site. In the van den Honert and Mortimer technique, a counter-current is applied on only one side of the electrode, which counter-current is of a sufficient magnitude to block propagation of the action potential in that direction from the excitation site. In the Fang and Mortimer technique, the counter-current is regulated to block large diameter nerve fibers while permitting the action potentials on the small diameter fibers to propagate past the end of the electrode. The action potentials propagating on the unblocked small diameter fibers cause flexing of the hind leg muscles with proportionately less force and less fatigue.

The present invention contemplates a new and improved technique for differentiating action potentials destined for different organs.

SUMMARY OF THE INVENTION

In accordance with one aspect of the present invention, a technique is provided for differentiating among action potentials travelling along a common nerve bundle which are destined for different end organs.

In accordance with one aspect of the present invention, action potentials are generated on nerve fibers connected with both the first and second end organs. The action potentials travelling to one of the end organs are blocked.

In accordance With another aspect of the present invention, an electrode is placed around the nerve bundle. Electrical currents are applied to the electrode such that action potentials are generated and travel from the electrode on the nerve fibers associated with a selectable one of the end organs.

In accordance with another aspect of the present invention, a method of controlling bladder draining is provided. Action potentials are initiated on a nerve bundle which includes nerve fibers flowing to detrusor muscles and to the urethral sphincter. Action potentials are caused to emanate from the electrode upstream toward the spinal cord on at least the nerve fibers destined for the urethral sphincter muscle for collision blocking action potentials coming from the spinal cord such that the urethral sphincter is allowed to relax. Concurrently, action potentials are produced flowing downstream on the nerve fibers connected with the detrusor muscles but not on the nerve fibers connected with the urethral sphincter.

One advantage of the present invention is that it enables action potentials to be created selectively on portions of a nerve bundle.

Another advantage of the present invention is that it enables action potentials to be transmitted along a subgroup of nerve fibers within a bundle, which subgroup is connected with a first end organ or muscle to the exclusion of nerve fibers associated with another end organ.

Another advantage of the present invention is that it enables the bladder to be drained without operating detrusor and sphincter muscles at cross purposes.

Still further advantages of the present invention will become apparent from the following detailed description.

BRIEF DESCRIPTION OF THE DRAWINGS

The invention may take in form in various parts and arrangements of parts, and in various steps and arrangements of steps. The drawings are only for purposes of illustrating the invention and are not to be construed as limiting it.

DETAILED DESCRIPTION OF THE PREFERRED EMBODIMENT

Figure 1:
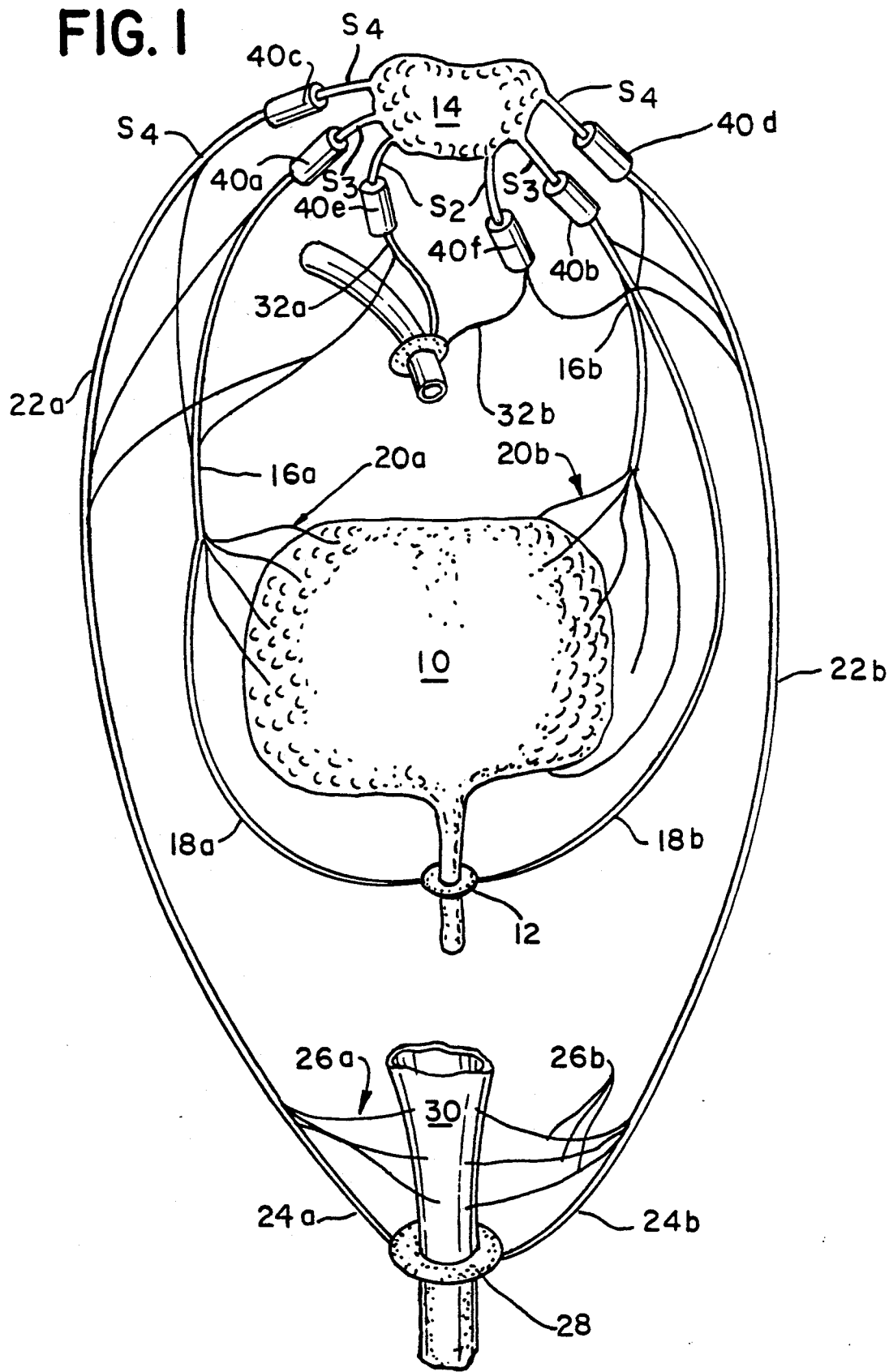
FIG. 1 is a diagrammatic illustration illustrating the placement of electrodes for control of the bladder and other organs.

With reference to FIG. 1, various lower abdominal organs are controlled by action potentials that travel from the brain, through the spinal cord, and through sacral ventral roots to the end organs. More specifically, action potentials traveling along the $S_2$, $S_3$, and $S_4$ sacral ventral roots control penile erection, bladder evacuation, and defecation.

Looking first to bladder evacuation, the bladder 10 and urethral sphincter 12 are controlled by action potentials traveling from the spinal cord 14 primarily, but not limited to, on a left-right symmetric pair of $S_3$ sacral ventral roots.

The $S_3$ ventral roots include bundles 16a, 16b of nerve fibers including larger diameter fibers 18a, 18b and smaller diameter fibers 20a, 20b. The larger diameter fibers connect between the spinal cord 14 and the urethral sphincter 12. Action potentials flowing along the larger diameter nerve fibers cause the urethral sphincter to contract, blocking the outlet from the bladder 10. In a healthy person, the brain causes a regular stream of action potentials flowing along the larger diameter fibers 18a, 18b to keep the urethral sphincter contracted. When the bladder is to be emptied, the flow of action potentials through the larger diameter nerve fibers is stopped allowing the sphincter to relax.

The smaller nerve fibers 20a, 20b connect between the spinal cord and the bladder, particularly the detrusor muscle layer which causes the bladder to contract. In a healthy person, the smaller diameter fibers usually carry no action potentials until the person desires to evacuate the bladder. To evacuate the bladder, action potentials are sent along the smaller diameter nerve fibers 20a, 20b concurrently with the stopping of sending action potentials along the larger diameter nerve fibers 18a, 18b. This causes the urethral sphincter to relax and allow the bladder outlet to open concurrently with detrusor contracting to expel urine.

Analogously, the $S_3$ and $S_4$ sacral ventral roots and to a lesser extent the $S_2$ sacral ventral roots provide nerve fibers which define bundles 22a, 22b of large diameter nerve fibers 24a, 24b and smaller diameter nerve fibers 26a, 26b. The large diameter nerve fibers control an anal sphincter muscle 28 and the small diameter fibers 26a, 26b control muscles which cause contraction around the rectal canal 30. Defecation is accomplished by concurrently terminating the supply of action potentials to the sphincter 28 allowing it to relax while smaller diameter nerve fibers 26a, 26b carry action potentials to the muscles which cause the rectal canal 30 to contract.

Analogously, bundles of nerve fibers 32a, 32b primarily from the $S_2$ ventral roots control penile erection.

Spinal cord injuries and various other medical conditions can cause a loss of control of these organs. To reinstitute this control, a cuff electrode 40, is mounted surrounding each of the appropriate sacral ventral roots. The cuff electrodes are configured for electrically exciting action potentials on the small diameter nerve fibers while blocking naturally occurring and electrically activated action potentials from traveling downstream on the larger diameter nerves. Specifically, electrodes 40a, 40b are implanted surrounding the $S_3$ roots to excite action potentials which activate the detrusor while blocking the transmission of action potentials on large diameter nerve fibers 18a, 18b to allow the sphincter 12 to relax. Analogously, electrodes 40c, 40d are surgically implanted around the $S_4$ roots. Electrodes 40e, 40f are implanted around the $S_2$ roots to control penile erection.

Figure 2:
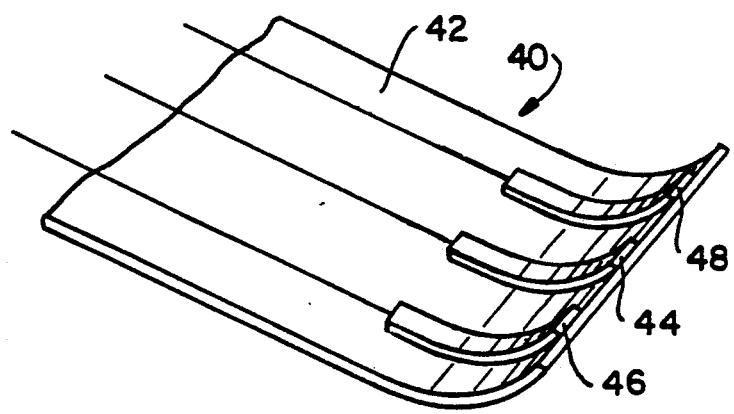
FIG. 2 is a perspective view illustrating electrode construction.
Figure 3:
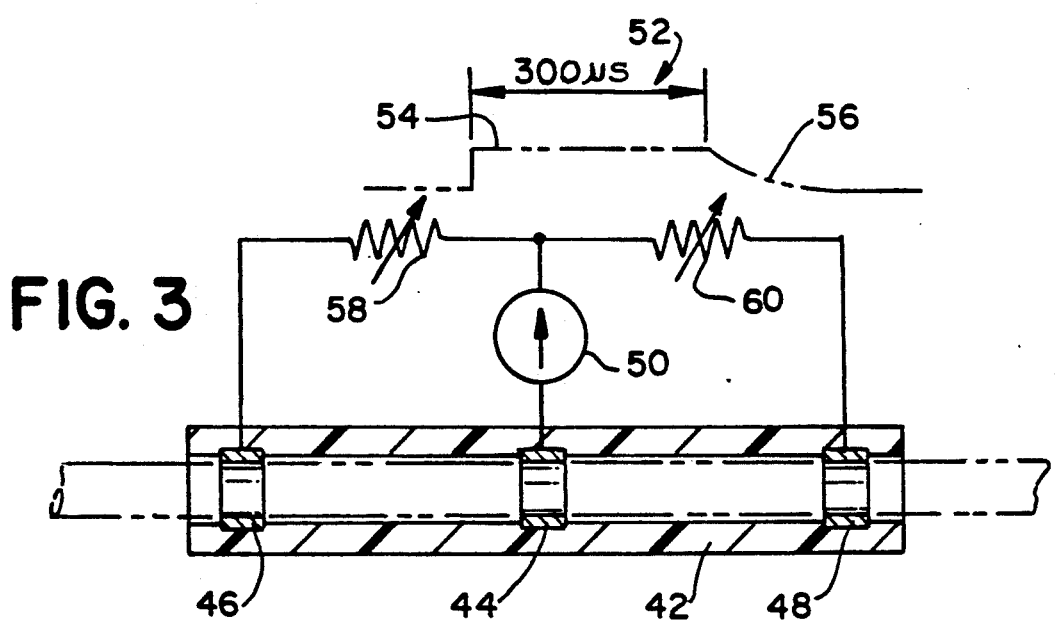
FIG. 3 is a detailed, cross-sectional illustration of one of the electrodes of FIG. 1; and, FIG. 4 is a graphic representation of blocking threshold versus fiber diameter.

With particular reference to FIGS. 2 and 3, each of the electrodes is a tripolar electrode. Preferably, the electrode is a self-curling spiral electrode that is biased to curl around the selected root analogous to the electrode illustrated in U.S. Pat. No. 4,602,624. The cuff electrode 40 has an insulator layer 42 that is biased to curl around the associated nerve root. In its coiled configuration, the layer 42 has an internal diameter very close to that of the diameter of the nerve root. For example, for a nerve root or trunk of about 1.0 mm diameter, an inner cuff diameter of 1.0 mm is preferred. Preferably, the cuff wraps 1.5–2 times around the nerve to prevent current leakage while having sufficiently few wraps that it is still easy to install.

The cuff electrode includes a central stimulating contact 44, an upstream end contact 46 toward the spinal cord, and a downstream end contact 48 toward the controlled organ. Each contact surface is defined by a thin, (preferably about 0.5 mm) wide strip of conductive film, e.g. platinum, iridium oxide, titanium oxide, or the like. In the coiled configuration, each strip forms an annular electrical contact partially or completely surrounding the nerve root.

The spacing between the annular electrodes is selected in accordance with the relative sizes of the nerve fibers. The spacing is selected such that there are about 3 to 4 nodes of the larger diameter fibers between each pair of electrode rings. The internodal length is generally about 100 times the fiber diameter. For example, a 20 $\mu$m diameter fiber has an internode length of about 2 mm. Analogously, a 10 $\mu$m fiber has an internodal length of about 1 mm. In the preferred embodiment, the cuff electrode is about 20 mm long with the electrode rings spaced about 6 to 8 mm apart. Action potentials propagate from node to node. When a node is momentarily depolarized with an electrical stimulus, an action potential starts propagating both upstream and downstream. When a region of nerve is subject to a sufficient hyperpolarization, it cannot pass an action potential and the action potential dies out or is blocked.

In the preferred embodiment, a current source 50 applies a quasi-trapezoidal shaped stimulus current pulse 56 between the central electrical contact 44 and the two end contacts 46 and 48. The pulse has a sufficient amplitude at its leading edge to depolarize the nodes of both large and small diameter nerve fibers (depolarize from the resting state by about −25 mV across the membranes of the nodes) and initiate action potentials propagating bidirectionally therealong. The current pulse has a flat plateau 54 on the order of 300–500 μs that hyperpolarizes the nodes of the nerve fibers in the region of electrodes placed at the ends of the cuff, 46, 48. The amplitude of the current pulse is selected such that a hyperpolarizing potential of about 55 mV more negative than the resting potential is created across the nodes of the larger diameter nerve fibers on which action potentials are to be blocked. A smaller magnitude potential is created across the nodes of the smaller diameter nerve fiber on which action potentials will be permitted to pass. It will be noted that less electrical current is required to lower the potential at the nodes of the larger diameter fiber than at the nodes of the smaller diameter fiber because spacing nodes is greater for large diameter nerve fibers than for small diameter fibers. The amplitude of the plateau is adjustable to select which diameters of nerve fibers will be hyperpolarized to a blocking level. Raising the plateau amplitude increases the hyperpolarization to block progressively smaller diameter nerve fibers. An exponentially decaying tail 56 prevents the anodal break phenomenon. Variable resistor elements 58 and 60 are included to create a current distribution that would permit action potentials to be blocked in one direction but not the other (e.g. allowed to pass in the upstream direction but blocked from travelling downstream at the downstream electrode or to tune the blocking effect because the current is higher at the downstream electrode).

Figure 4:
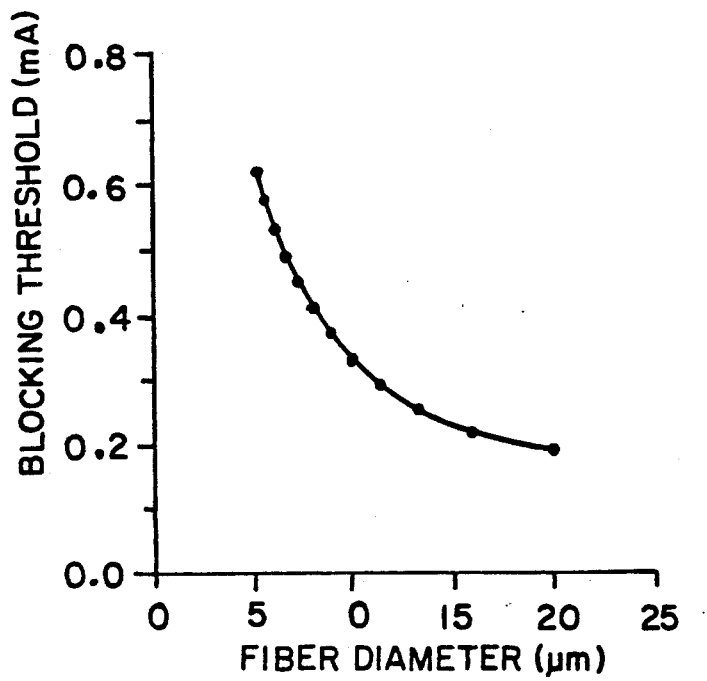

FIG. 4 illustrates the relationship between the nerve fiber diameter and the minimum current from the blocking current source 50 necessary to block the movement of action potentials in the nerve fibers with different diameters. For example, a blocking current of about 0.325 mA blocks the flow of action potentials in nerve fibers having a diameter of about 10 μm or larger. Analogously, FIG. 4 describes the blocking current to be supplied for other diameters between which one may wish to discriminate.

In the preferred embodiment, the excitation pulse 52 from current source 50 has a sufficient magnitude to excite action potential in nerves of all sizes present in the bundle or root. As with the blocking potential, the amount of current necessary to excite action potentials is higher in smaller diameter fibers than in larger diameter fibers. Thus, by appropriately sizing the excitation current pulse, action potentials can be selectively generated only in nerve fibers greater than a selected, corresponding diameter. This technique may find application in sending signals only to the urethral sphincter to contract the sphincter while allowing the bladder detrusor muscles to relax when the bladder is not to be emptied.

Electrodes 40c, 40d on the S4 ventral root are controlled analogously to cause action potentials on the smaller nerve fibers of the appropriate diameter for exciting the contracting musculature while blocking action potentials on the larger diameter nerve fibers to relax the external sphincter to cause defecation. Electrodes 40e, 40f are controlled to relax arterial control muscles.

This technique may be used to differentiate among other organs or muscle groups. The invention may find application in conjunction with other motor or sensory nerves. For example, by passing action potentials on different size nerve fibers of the auditory nerve, different tones can be communicated to the brain. Analogously, other information may be input into the brain by selectively exciting action potentials in other afferent nerve fibers of selected diameter ranges.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A method of controlling bladder discharge in which detrusor activation for contracting the bladder is controlled by action potentials passing along smaller diameter nerve fibers of a sacral root and in which contraction of a urethral sphincter for closing an outlet from the bladder is caused by action potentials passing along larger diameter nerve fibers of the sacral root, the method of controlling bladder discharge comprising:

electrically exciting action potentials on at least the smaller diameter nerve fibers, whereby the detrusor is activated to cause contraction of the bladder;

concurrently blocking action potentials from passing along the larger diameter nerve fibers, whereby the urethral sphincter is permitted to relax.

2. The method as set forth in claim 1 wherein:

the step of exciting action potentials includes exciting action potentials on both the larger and smaller diameter nerve fibers concurrently at an excitation location; and the blocking step includes blocking action potentials on the larger diameter nerve fibers propagating downstream from the excitation location.

3. The method as set forth in claim 2 wherein the action potential exciting step further includes:

exciting action potentials that propagate both upstream and downstream from the excitation location on both the larger and smaller diameter nerve fibers such that the excited action potentials travelling upstream collision block any naturally occurring action potentials travelling downstream from the spinal cord and those travelling downstream, from the excitation location, on the larger diameter nerve fibers are blocked at the downstream electrode.

4. The method as set forth in claim 2 further including:

implanting around the sacral root a cuff electrode which has a central electrical contact, an upstream end electrical contact upstream from the central contact, and a downstream end electrical contact downstream from the central contact toward the detrusor and the urinary sphincter;

wherein the excitation step includes applying a stimulus current pulse between the end and central electrical contacts and the blocking step includes holding the applied stimulus pulse long enough to block passage of the action potential on larger fibers at the end contacts.

5. The method as set forth in claim 4 further including selectively adjusting an amplitude of the current pulse for selectively adjusting a diameter of nerve fibers along which the propagation of action potentials is blocked.

6. The method as set forth in claim 5 further including:
   implanting a second electrode on another sacral root which has larger diameter nerve fibers connected with an anal sphincter muscle and smaller diameter fibers connected with musculature for contracting a rectal canal during defecation, the second electrode having at least a second central electrical contact, a second upstream end electrical contact, and a second downstream end electrical contact;
   applying an electrical current pulse between the end and central electrical contacts which excites action potentials in both the large and small diameter nerve fibers of the another sacral root and which selectively block action potentials on the larger diameter nerve fibers of the another sacral root, whereby the blocking of action potentials on the larger diameter nerve fibers causes the anal sphincter muscle to relax and action potentials passing along the smaller diameter nerve fibers cause contraction of the rectal canal.

7. The method as set forth in claim 6 further including:
   implanting a third electrode on a third sacral root which controls penile erections, the third electrode including at least two electrical contacts;
   selectively applying a current pulse between the two electrical contacts to induce action potentials to propagate along the third sacral root, which induced action potentials cause a penile erection.

8. A method of selectively, concurrently exciting and blocking the excitation of first and second end organs which are controlled by small and large diameter nerve fibers, respectively, of a common nerve trunk, the method comprising:
   electrically exciting action potentials on at least the smaller diameter nerve fibers;
   concurrently blocking action potentials from passing along the larger diameter nerve fibers toward the second end organ.

9. The method as set forth in claim 8 wherein
   the step of electrically exciting action potentials includes exciting action potentials on both the larger and smaller diameter nerve fibers concurrently at an excitation location; and
   the blocking step includes blocking action potentials on only the larger diameter nerve fibers from propagating downstream from the excitation location.

10. The method as set forth in claim 9 wherein the action potential exciting step further includes exciting action potentials that propagate in both orthodromic and antidromic directions on both the large and small diameter nerve fibers such that the electrically excited action potentials travelling in the antidromic direction collision block naturally occurring action potentials travelling in the orthodromic direction on the larger diameter nerve fibers.

11. The method as set forth in claim 9 further including:
   implanting a cuff electrode around the nerve trunk which electrode has a central electrical contact, an upstream end electrical contact upstream from the central contact, and a downstream end electrical contact;
   wherein the excitation step includes applying a current pulse between the end contacts and central electrical contacts and the blocking step includes continuing to apply current pulse between the end contacts and central electrical contacts for a sufficient duration to hold internodes of the large diameter nerve fibers hyperpolarized until all action potentials initiated on the larger diameter nerve fibers by initially applying the current pulse are blocked.

12. The method as set forth in claim 11 further including selectively adjusting an amplitude of the current pulse for selectively adjusting a diameter of nerve fibers along which the propagation of action potentials is blocked.

13. An electrical system for selectively controlling evacuation of a patient's bladder by concurrently generating action potentials on smaller diameter nerve fibers which cause contraction of the patient's bladder and suppressing action potentials in larger diameter nerve fibers connected with the patient's urethral sphincter to allow the urethral sphincter to relax, the larger and smaller diameter nerve fibers originating in part in left and right $S_2$ sacral roots, left and right $S_3$ sacral roots, and left and right $S_4$ sacral roots, the electrical system comprising:
   a first cuff electrode at least partially encircling the left $S_3$ sacral root;
   a second cuff electrode at least partially encircling the right $S_3$ sacral root;
   a third cuff electrode at least partially encircling the left $S_4$ sacral root;
   a fourth cuff electrode at least partially encircling the right $S_4$ sacral root;
   each of the first, second, third, and fourth cuff electrodes including a central electrical contact, an antidromic end electrical contact, and an orthodromic end electrical contact, each of the cuff electrodes being implanted at least partially encircling the respective root with its antidromic end disposed closer to the patient's spinal column than its orthodromic end;
   a current source means connected between the end electrical connectors and the central electrical connector of each cuff electrode for selectively applying quasi-trapezoidal shaped current pulses have a generally flat plateau and an exponentially decaying tail;
   a means for adjusting an amplitude of the current pulses such that (i) a substantially −25 millivolt potential relative to a resting potential is created across membranes of nodes of the larger and smaller diameter nerve fibers to depolarize the nodes and initiate propagation of action potentials on the larger and smaller diameter nerve fibers and (ii) a hyperpolarizing potential of about 55 millivolts more negative than the resting potential is created across the nodes of the larger diameter nerve fibers blocking orthodromic propagation of action potentials on the larger diameter fibers without blocking orthodromic action potential propagation on the smaller diameter nerve fibers.

* * * * *